United States Patent [19]
Wallach

[11] Patent Number: 5,147,723
[45] Date of Patent: * Sep. 15, 1992

[54] PAUCILAMELLAR LIPID VESICLES

[75] Inventor: Donald F. H. Wallach, Brookline, Mass.

[73] Assignee: Micro-Pak, Inc., Wilmington, Del.

[*] Notice: The portion of the term of this patent subsequent to Aug. 8, 2006 has been disclaimed.

[21] Appl. No.: 443,516

[22] Filed: Nov. 29, 1989

Related U.S. Application Data

[63] Continuation of Ser. No. 157,571, Mar. 3, 1988, Pat. No. 4,911,928, which is a continuation-in-part of Ser. No. 25,525, Mar. 13, 1987, abandoned, and a continuation-in-part of Ser. No. 78,658, Jul. 28, 1987, Pat. No. 4,855,090, and a continuation-in-part of Ser. No. 124,824, Nov. 25, 1987, Pat. No. 4,917,951.

[51] Int. Cl.$^5$ .................... A61K 9/127; B01J 13/02
[52] U.S. Cl. .................... 428/402.2; 264/4.1; 424/89; 424/420; 424/450; 436/829; 514/6; 514/963; 525/936
[58] Field of Search .............. 264/4.1; 428/402.2; 424/420, 450; 525/936; 436/829; 514/963

[56] References Cited

U.S. PATENT DOCUMENTS

| | | | |
|---|---|---|---|
| 4,217,344 | 8/1980 | Vanlerberghe et al. | 424/60 |
| 4,247,411 | 1/1981 | Vanlerberghe et al. | 264/4.6 |
| 4,855,090 | 8/1989 | Wallach | 264/4.1 |
| 4,911,928 | 3/1990 | Wallach | 424/450 |
| 4,917,951 | 4/1990 | Wallach | 428/402.2 |

OTHER PUBLICATIONS

Grant & Hackh's *Chemical Dictionary*, 5th Ed. (1987), p. 462.
"Les Niosomes", Handjani-Vila et al., *Les Liposomes*, Puisieux and Delatire, Eds., Techniques Et Documentation La Voisier Paris, pp. 297-313 (1985).

*Primary Examiner*—Richard D. Lovering
*Attorney, Agent, or Firm*—Lahive & Cockfield

[57] ABSTRACT

A new method of producing paucilamellar lipid vesicles has been developed. The vesicles are made of non-phospholipid surfactants. The paucilamellar lipid vesicles have 2-8 lipid bilayers surrounding a central cavity which may be filled with either an aqueous-based solution or an oil or wax.

25 Claims, 1 Drawing Sheet

PAUCILAMELLAR LIPID VESICLES

REFERENCE TO RELATED APPLICATIONS

This is a continuation of application Ser. No. 157,571, now U.S. Pat. No. 4,911,928, filed Mar. 3, 1988 which is a continuation-in-part of U.S. patent application Ser. No. 025,525, filed Mar. 13, 1987, entitled "Method of Producing High Aqueous Volume Multilamellar Vesicles", now abandoned, U.S. patent application Ser. No. 078,658, filed Jul. 28, 1987, also entitled "Method of Producing High Aqueous Volume Multilamellar Vesicles", now U.S. Pat. No. 4,855,090; and U.S. patent application Ser. No. 124,824, filed Nov. 25, 1987, entitled "Lipid Vesicles Formed of Surfactants and Steroids", now U.S. Pat. No. 4,917,951.

This application is also related to U.S. patent application Ser. No. 163,806, filed even date herewith, entitled "Method and Apparatus for Producing Lipid Vesicles", U.S. Pat. No. 4,895,452.

BACKGROUND OF THE INVENTION

The present invention relates to the production of paucilamellar lipid vesicles. More particularly, the present invention relates to a method of producing paucilamellar lipid vesicles having an aqueous or organic amorphous liquid or solid central cavity. These paucilamellar lipid vesicles have a wide variety of non-phospholipid surfactants as their primary structural material, with a small amount of phospholipid added if desired.

Lipid vesicles are substantially spherical structures made of materials having a high lipid content, e.g., surfactants or phospholipids. The lipids of these spherical vesicles are organized in the form of lipid bilayers. The lipid bilayers encapsulate an aqueous volume which is either interspersed between multiple onion-like shells of lipid bilayers (forming multilamellar lipid vesicles or "MLV") or the aqueous volume is contained within an amorphous central cavity. The most commonly known lipid vesicles having an amorphous central cavity filled with aqueous medium are the unilamellar lipid vesicles. Large unilamellar vesicles ("LUV") generally have a diameter greater than about 1μ while small unilamellar lipid vesicles ("SUV") generally have a diameter of less than 0.2μ. There are a variety of uses for lipid vesicles including the use as adjuvants or as carriers for a wide variety of materials.

Although substantially all the investigation of lipid vesicles in recent years has centered on multilamellar and the two types of unilamellar lipid vesicles, a fourth type of lipid vesicle, the paucilamellar lipid vesicle ("PLV"), exists. This lipid vesicle has barely been studied heretofore and has only been manufactured previously with phospholipids. PLV's consist of about 2 to 8 peripheral bilayers surrounding a large, unstructured central cavity. In all the previously described PLV's, this central cavity was filled with an aqueous solution. See Callo and McGrath, Cryobiology 1985, 22(3), pp. 251-267.

Each type of lipid vesicle appears to have certain uses for which it is best adapted. For example, MLV's have a higher lipid content then any of the other lipid vesicles so to the extent that a lipid vesicle can encapsulate or carry a lipophilic material in the bilayers without degradation, MLV's have been deemed the most advantageous for carrying lipophilic materials. In contrast, the amount of water encapsulated in the aqueous shells between the lipid bilayers of the MLV's is much smaller than the water which can be encapsulated in the central cavity of LUV's, so LUV's have been considered advantageous in transport of aqueous material. However, LUV's, because of their single lipid bilayer structure, are not as physically durable as MLV's and are more subject to enzymatic degradation. SUV's have neither the lipid or aqueous volumes of the MLV's or LUV's but because of their small size have easiest access to cells in tissues.

PLV's, which can be considered a sub-class of the MLV's, are a hybrid having features of both MLV's and LUV's. PLV's appear to have advantages as transport vehicles for many uses as compared with the other types of lipid vesicles. In particular, because of the large unstructured central cavity, PLV's are easily adaptable for transport of large quantities of aqueous-based materials. However, the multiple lipid bilayers of the PLV's provides PLV's with the capacity to transport a greater amount of lipophilic material in their bilayers as well as with additional physical strength and resistance to degradation as compared with the single lipid bilayer of the LUV's. As illustrated in the present application, the aqueous cavity of the PLV's can be filled wholly or in part with an apolar oil or wax and then can be used as a vehicle for the transport or storage of hydrophobic materials. The amount of hydrophobic material which can be transported by the PLV's with an apolar core is much greater than can be transported by MLV's.

Conventional multilamellar lipid vesicle producing methods start by dissolving the lipids, together with any lipophilic additives, in an organic solvent. The organic solvent is then removed by evaporation using heat or by passing a stream of an inert gas (e.g., nitrogen) over the dissolved lipids. The residue is then hydrated with an aqueous phase, generally containing electrolytes and additives such as hydrophilic biologically-active materials, to form large multilamellar lipid membrane structures. In some variations, different types of particulate matter or structures have been used during the evaporation process to assist in the formation of the lipid residue. Those in the field have shown that by changing the physical structure of the lipid residue, better vesicles form upon hydration. Two recent review publications, Gregoriadis, G., ed. *Liposome Technology* (CRC, Boca Raton, Fla.), Vols. 1-3 (1984), and Dousset and Douste-Blazy (in *Les Liposomes*, Puisieux and Delattre, Editors, Techniques et Documentation Lavoisier, Paris, pp. 41-73 (1985)), summarize the methods which have been used to make MLV's. Phospholipid PLV's have been made by minor modifications of these processes.

No matter how the MLV's or PLV's are formed, once made it is necessary to determine the effectiveness of the process. Two measurements commonly used to determine the effectiveness of encapsulation of materials in lipid vesicles are the encapsulated mass and captured volume. The encapsulated mass is the mass of the substance encapsulated per unit mass of the lipid and is often given as a percentage. The captured volume is defined as the amount of the aqueous phase trapped inside the vesicle divided by the amount of lipid in the vesicle structure, normally given in ml liquid/g lipid.

All of the early lipid vesicle or liposome studies used phospholipids as the lipid source for the bilayers. The reason for this choice was that phospholipids are the principal structural components of natural membranes. However, there are many problems using phospholipids as artificial membranes. First, isolated phospholipids are subject to degradation by a large variety of enzymes. Second, the most easily available phospholipids are those from natural sources, e.g., egg yolk lecithin, which contain polyunsaturated acyl chains that are subject to autocatalyzed peroxidation. When peroxidation occurs, the lipid structure breaks down, causing premature release of encapsulated materials and the formation of toxic peroxidation byproducts. This problem can be avoided by hydrogenation but hydrogenation is an expensive process, thereby raising the cost of the starting materials. Cost is a third problem associated with the use of phospholipids on a large scale. A kilogram of egg yolk lecithin pure enough for pharmacological liposome production presently costs in excess of $1,000. This is much to high a cost for a starting material for most applications.

Recently, there has been some indication, particularly from the L'Oreal group, that commercially available surfactants might be used to form the lipid bilayer in liposome-like multilamellar lipid vesicles. Both surfactants and phospholipids are amphiphiles, having at least one lipophilic acyl or alkyl group attached to a hydrophilic head group. The head groups are attached to one or more lipophilic chains by ester or ether linkages. Commercially available surfactants include the BRIJ family of polyoxyethylene acyl ethers, the SPAN sorbitan alkyl esters, and the TWEEN polyoxyethylene sorbitan fatty acid esters, all available from ICI Americas, Inc. of Wilmington, Del.

The methods and materials disclosed herein for producing the paucilamellar lipid vesicles all yield vesicles with a high aqueous or oil volume. Electron micrographs confirm that the paucilamellar lipid vesicles are distinct from the LUV's and the classic MLV's.

Accordingly, an object of the invention is to provide paucilamellar lipid vesicles from non-phospholipid materials.

Another object of the invention is to provide a method of producing paucilamellar lipid vesicles which is rapid and uses relatively inexpensive materials.

A further object of the invention is to provide a method of manufacturing vesicles having a membrane-like outer structure surrounding an oil or fat droplet.

An additional object of the invention is to provide a vehicle for transport of oil soluble materials.

These and other objects and features of the invention will be apparent from the detailed description and the claims.

SUMMARY OF THE INVENTION

The present invention features paucilamellar lipid vesicles for use as carriers of either hydrophilic or hydrophobic materials, and a method for their manufacture. The invention further features the use of paucilamellar lipid vesicles to encapsulate and transport a broad spectrum of materials.

The method of the present invention for making paucilamellar lipid vesicles has the steps of forming a lipophilic phase of a surfactant and any lipid soluble materials being encapsulated which are dissoluble in the surfactant. The surfactants are selected from a group consisting of polyoxyethylene fatty esters having the formula $$R_1-COO(C_2H_4O)_nH$$

where $R_1$ is lauric, myristic, cetyl, stearic, or oleic acid, or their derivatives and $n=2-10$; polyoxyethylene fatty acid ethers, having the formula $$R_2-CO(C_2H_4O)_mH$$

where $R_2$ is lauric, myristic, or cetyl acids or their derivatives, single or double unsaturated octadecyl acids or their derivative, or double unsaturated eicodienoic acids or their derivatives and m ranges from 2–4; diethanolamines, having the formula $$(HOCH_2-CH_2)_2NCO-R_3$$

where $R_3$ is caprylic, lauric, myristic or linoleic acids or their derivatives;

long chain acyl hexosamides having the formula $$R_4-NOCO-(CH_2)_b-CH_3$$

where b ranges from 10–18 and $R_4$ is a sugar molecule selected from a group consisting of glucosamine, galactosamine, and N-methylglucamine;

long chain acyl amino acid amides having the formula $$R_5-CHCOOH-NOC-(CH_2)_c-CH_3$$

where c ranges from 10–18 and $R_5$ is an amino acid side chain;

long chain acyl amides having the formula $$HOOC-(CH_2)_d-N(CH_3)_2-(CH_2)_3-NCO-R_6$$

where $R_6$ is an acyl chain having 12–20 carbons and not more than two unsaturations, and d ranges from 1–3;

polyoxyethylene (20) sorbitan mono- or trioleate;

polyoxyethylene glyceryl monostearate with 1–10 polyoxyethylene groups;

and glycerol monostearate.

The lipophilic phase is blended with an aqueous phase consisting of an aqueous buffer and any aqueous soluble materials to be encapsulated, under shear mixing conditions, to form the paucilamellar lipid vesicles. "Shear mixing" is defined as the mixing of the lipophilic phase with the aqueous phase under turbulent or shear conditions which provide adequate mixing to hydrate the lipid and form lipid vesicles. The pump speeds are modified depending on the viscosity of the materials and the size of the orifices selected. "Shear mixing" is achieved by liquid shear which is substantially equivalent to a relative flow rate for the combined phases of about 5–30 m/s through a 1 mm radius orifice.

The invention further features the encapsulation of oil-soluble or oil-suspendable materials within paucilamellar lipid vesicles. This procedure commences with dispersing the material to be encapsulated in an oil or wax forming an oily phase. The oil or wax is a water immiscible oily solution selected from a group consisting of oils, waxes, natural and synthetic triglycerides, acyl esters, and petroleum derivatives, and their analogues and derivatives. The terms "disperse" or "dispersion" as used herein include dissolution or forming a suspension or colloid to yield a flowable phase. The oily phase containing the oil-dispersible material is mixed with the lipid phase and the combined oil-lipid phase is blended under shear mixing conditions with the aqueous phase. Surfactants useful in the encapsulation process are the same as those used to make paucilamellar lipid vesicles with an aqueous core.

In preferred embodiments of the invention, charge producing materials and steroids such as cholesterol or hydrocortisone or their analogues and derivatives are used in the formation of the paucilamellar lipid vesicles. Preferred charge producing materials are negative charge producing materials such as dicetyl phosphate, cetyl sulphate, phosphatidic acid, phosphatidyl serine, oleic acid, palmitic acid, or mixtures thereof.

In order to achieve the proper blending necessary to form the paucilamellar lipid vesicles, all of the materials are normally in a flowable state. However, in the process of the present invention, use of a solvent for the surfactant (the classic method of producing multilamellar lipid vesicles) is not only unnecessary; it is counterproductive. Many of the surfactants useful in the invention are liquids at room temperature or at slightly elevated temperatures so only gentle heating is necessary for flowability. Even the most difficult surfactants of the group to use, e.g., glycerol monostearate, can be easily handled at approximately 70° C. Therefore, one standard procedure of the invention is to elevate the temperature of the lipophilic phase in order to make it flowable followed by carrying out the shear mixing between the lipophilic phase and the aqueous phase at a temperature such that both phases are liquids. While it is often desirable to use the same temperature for both phases, this is not always necessary.

DETAILED DESCRIPTION OF PREFERRED EMBODIMENTS

Figure 1:
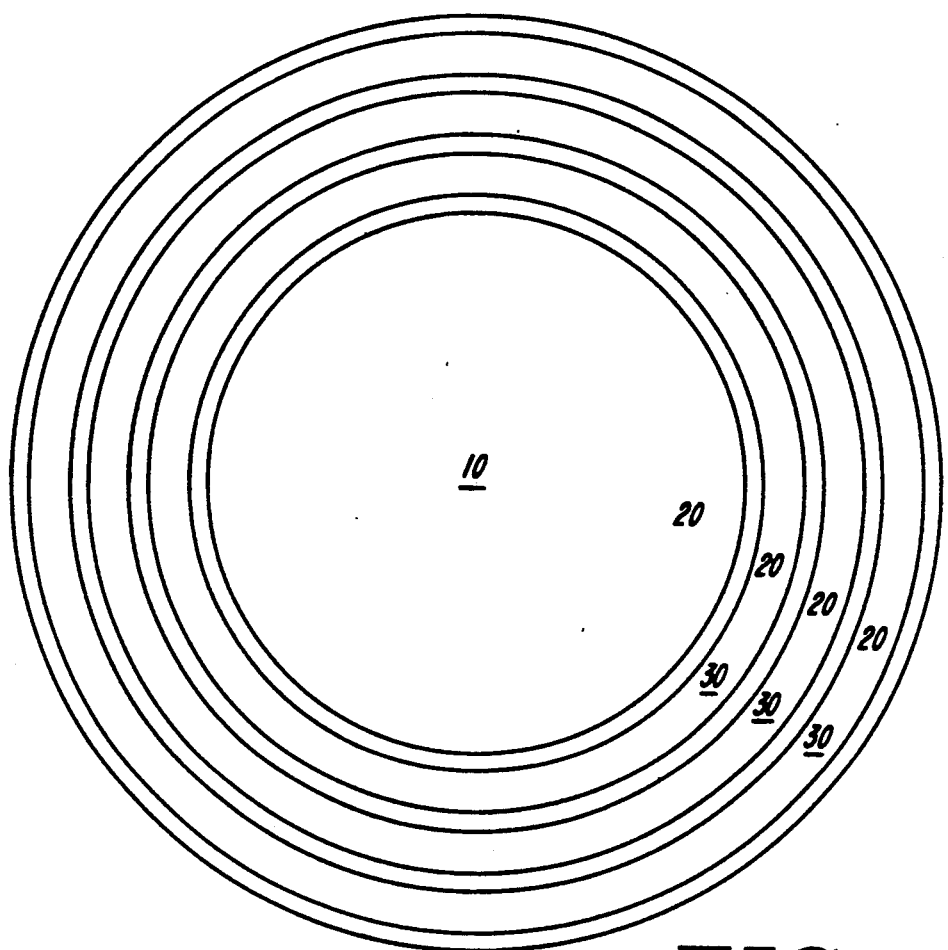
FIG. 1 is a schematic illustration of a paucilamellar lipid vesicle of the invention.

The present invention relates to the production of paucilamellar lipid vesicles and the paucilamellar lipid vesicles themselves. These lipid vesicles, which are formed of non-phospholipid surfactant material, are characterized by 2–8 lipid bilayers with a small aqueous volume separating each substantially spherical lipid shell. The lipid bilayers surround an amorphous central cavity. The cavity can be filled with an oil (including a wax), an aqueous-based solution or some mixture thereof. These paucilamellar lipid vesicles are capable of being used as drug or vaccine transport devices, adjuvants, or carriers of other types of organic or non-organic material. In fact, these lipid vesicles can be used where microcapsules or other types of non-lipid carriers have previously been used, e.g., as paint or dye carriers.

For certain uses, the incorporation of a charge producing amphiphile, yielding a net positive or negative charge to the lipid vesicles, is helpful. The preferred negative charge producing materials are oleic acid, dicetayl phosphate, palmitic acid, cetyl sulphate, retinoic acid, phosphatidic acid, phosphatidyl serine, and mixtures thereof. In order to provide a net positive charge to the vesicles, long chain amines, e.g., stearyl amines or oleyl amines, long chain pyridinium compounds, e.g., cetyl pyridinium chloride, quaternary ammonium compounds, or mixtures of these can be used. A preferred positive charge producing material is hexadecyl trimethylammonium bromide, a potent disinfectant. The use of this disinfectant as the positive charge producing material within the vesicles provides a secondary advantage as the vesicles deteriorate; they act as a sustained release germicide carriers.

The vesicles may also include targeting molecules, either hydrophilic or amphiphilic, which can be used to direct the vesicles to a particular target in order to allow release of the material encapsulated in the vesicle at a specified biological location. If hydrophilic targeting molecules are used, they can be coupled directly or via a spacer to an OH residue of the polyoxyethylene portion of the surfactant, or they can be coupled, using state of the art procedures, to molecules such as palmitic acid, long chain amines, or phosphatidyl ethanolamine. If spacers are used, the targeting molecules can be interdigitated into the hydrophilic core of the bilayer membrane via the acyl chains of these compounds. Preferred hydrophilic targeting molecules include monoclonal antibodies, other immunoglobulins, lectins, and peptide hormones.

In addition to hydrophilic targeting molecules, it is also possible to use amphiphilic targeting molecules. Amphiphilic targeting molecules are normally not chemically coupled to the surfactant molecules but rather interact with the lipophilic or hydrophobic portions of the molecules constituting the bilayer lamellae of the lipid vesicles. Preferred amphiphilic targeting molecules are neutral glycolipids, galactocerebrosides (e.g., for hepatic galactosyl receptors), or changed glycolipids such as gangliosides.

Vesicles made using the methods of the present invention can be used in diagnostic testing, e.g., agglutination testing of immunological systems. The vesicles can also be used as markers or labels for visualization, e.g., swelling or shrinking in the presence of an immune reaction, or for radiography or NMR.

Hydrophilic materials which can be encapsulated include macromolecules, viruses, immunological adjuvants such as muramyl dipeptide, peptide hormones such as insulin, calcitonin and glucagon, hypothalmic peptides, pituitary hormones, growth factors such as angiogenic, epithelial and epidermal growth factors, lymphokines such as interleukin-2 and interferon, blood proteins such as hemoglobin and Factor VIII, water-soluble plant hormones and pesticides, radionucleotides, contrast materials for radiological and NMR diagnosis, cancer cytostatics, and antibiotics. Examples of lipophilic materials which can be encapsulated include steroid hormones, pheromones, porphyrins, organic pesticides, fungicides, insect repellants, and lipophilic vitamins and derivatives. Oil based materials include some additional lipophilic materials and materials which form colloids or suspensions in oil. A more complete listing of the types of pharmaceuticals that could be encapsulated in lipid vesicles is included in Gregoriadis, G., ed. *Liposome Technology* (CRC, Boca Raton, Fl.), Vols. 1–3 (1984).

The paucilamellar lipid vesicles can be made by a variety of devices which provides sufficiently high shear for shear mixing. There are a large variety of these devices available on the market including a microfluidizer such as is made by Biotechnology Development Corporation, a "French"-type press, or some other device which provides a high enough shear force and the ability to handle heated, semiviscous lipids. If a very high shear device is used, it may be possible to microemulsify powdered lipids, under pressure, at a temperature below their normal melting points and still form the lipid vesicles of the present invention.

A device which is particularly useful for making the lipid vesicles of the present invention has been developed by Micro Vesicular Systems, Inc., Vineland, N.J. and is further described in U.S. patent application Ser. No. 163,806, filed even date herewith, now U.S. Pat. No. 4,895,452. Briefly, this device has a substantially cylindrical mixing chamber with at least one tangentially located inlet orifice. One or more orifices lead to a reservoir for the lipophilic phase, mixed with an oil phase if lipid-core PLV's are to be formed, and at least one of the other orifices is attached to a reservoir for the aqueous phase. The different phases are driven into the cylindrical chamber through pumps, e.g., positive displacement pumps, and intersect in such a manner as to form a turbulent flow within the chamber. The paucilamellar lipid vesicles form rapidly, e.g., less than 1 second, and are removed from the chamber through an axially located discharge orifice. In a preferred embodimen, there are four tangentially located inlet orifices and the lipid and aqueous phases are drawn from reservoirs, through positive displacement pumps, to alternating orifices. The fluid stream through the tangential orifices is guided in a spiral flow path from each inlet or injection orifice to the discharge orifice. The flow paths are controlled by the orientation or placement of the inlet or injection orifices so as to create a mixing zone by the intersection of the streams of liquid. The pump speeds, as well as the orifice and feed line diameters, are selected to achieve proper shear mixing for lipid vesicle formation. As noted, in most circumstances, turbulent flow is selected to provide adequate mixing.

No matter what device is used to form the paucilamellar lipid vesicles, if proper shear mixing is achieved they have a structure similar to that illustrated in FIG. 1. The large, unstructured amorphous center 10 is surrounded by a plurality of lipid bilayers 20 having aqueous layers 30 interspersed there between. About four lipid bilayers is standard with 2-8 possible. The amorphous center 10 may be entirely filled with an aqueous material, e.g., a buffer and any aqueous material to be encapsulated, or may be partially or totally filled with an oily material, forming lipid-core PLV's. If an aqueous center is used, the paucilamellar lipid vesicles will normally range in diameter from about 0.5-5 μ while if an oily center is used, the size may increase to up to about 15-20 μ depending upon the amount of oil used.

Figure 2:
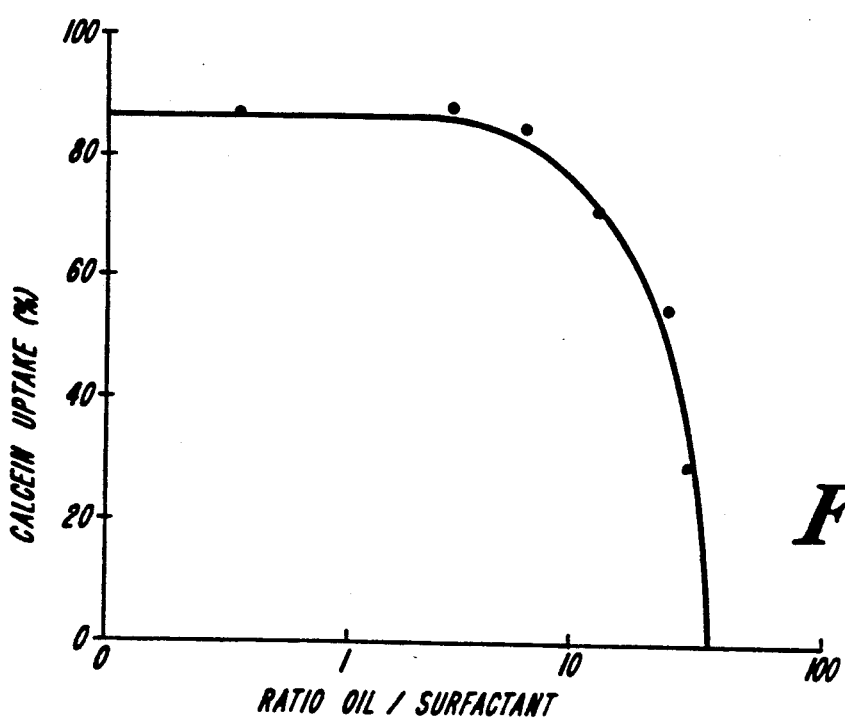
FIG. 2 is a graph of percent water uptake versus the oil-surfactant ratio using the dye calcein as an indicator of water uptake.

FIG. 2 illustrates the phenomena of oil displacing water from the vesicle. Approximately 2 ml of surfactant mixture forming the lipophilic phase, specifically, a 33/11/5 (M/M/M) polyoxyethylene (2) cetyl ether/cholesterol/oleic acid mixture, was mixed with different mineral oil volumes and then blended, using two syringes connected by a stopcock, with 3.0 ml of a phosphate buffered saline/calcein solution. The oil volumes ranged from 0 to 10 ml, resulting in a oil/surfactant mixture ratios (v/v) of 0-50. Calcein, which used as an indicator of the water uptake, was monitored by absorbance measurements at 485 nm and a volume correction which depended on the amount of oil was included to determine water uptake. FIG. 2 clearly shows that as the oil-surfactant ratio increased, the amount of calcein incorporated stayed substantially constant until the ratio reached about 4:1. As the ratio increased, the lipid vesicle increased in size as compared with the control (non-oil) vesicle. Increasing the ratio above 4:1 yields a decrease in the amount of calcein incorporated, showing that the surfactant bilayers had reached the end of their expansion capabilities and the oil was now driving the aqueous phase out of the lipid vesicle. As more and more oil is added, the calcein concentration decreases rapidly, indicating a loss of the aqueous phase from the center of the vesicle. At this stage, all of the aqueous phase is incorporated into the aqueous layers interspersed between the lipid bilayers and none remains in the central volume. When enough oil has been added so that the central volume can no longer hold it, the lipid vesicle begins to disintegrate.

Although it is not necessary for understanding the invention, it is theorized that a very small amount of the surfactant acts as a stabilizing agent, stabilizing the boundary between the aqueous volume and the oil volume, allowing the oil droplet to form. In fact, a small amount of a different surfactant can be used to assist in the formation of the paucilamellar lipid vesicles but this is not necessary since the surfactant that makes up the bilayers is sufficient for stability.

The oil core vesicles of the invention have the advantage that a large oil central volume can permit the encapsulation of large particles which are not dissolved in the oil but rather are in the form of suspensions or colloids. Particles such as paint pigments can be encapsulated in this manner.

The invention, and its many uses, will be more apparent from the following, non-limiting Examples.

EXAMPLE 1

The paucilamellar lipid vesicles of this Example were made using one of the most preferred materials, polyoxyethylene (2) cetyl ether. Although syringes were used to provide the shear mixing in this and most of the following Examples, any high shear device which provided sufficient shear mixing could be used.

TABLE 1

| | |
|---|---|
| Polyoxyethylene (2) cetyl ether | 0.696 gm |
| Cholesterol | 0.073 gm |
| Dicetyl phosphate | 0.055 gm |
| 5 mM phosphate, 150 mM NaCl, pH 7.4 | 10.0 ml |

Table 1 lists the materials and proportions used in preparing the lipid vesicles for this Example. The polyoxyethylene (2) cetyl ether, cholesterol and dicetyl phosphate were placed in a 5 ml syringe and heated to 40° C., a temperature above the melting point of the lipid. The dicetyl phosphate provided a net negative charge to the final membrane structure. The lipophilic phase which resulted after the heating and blending of the lipophilic components was forcibly injected, via a three-way stopcock, into an aqueous phase consisting of 10 ml of 5 mM phosphate buffer containing 150 mM NaCl, pH 7.4. The phosphate buffer, which was contained in a 25 ml syringe, was also at 40° C. The process of injection of the lipophilic phase into the aqueous phase took less than five seconds. The resulting mixture was then forced into a second 25 ml syringe at a linear flow rate of 8-12 m/s through an orifice about 1 mm in diameter. The mixture was driven continuously back and forth between the two 25 ml syringes for approximately 2 minutes, providing the shear mixing necessary to make the high volume paucilamellar lipid vesicles. A milky suspension containing the paucilamellar lipid vesicles resulted. The lipid vesicles were separated by centrifugation at 10,000 rpm for 15 minutes in a Beckman Instrumental Co. J-21 centrifuge, forming a low density phase on top of the aqueous solution.

The paucilamellar lipid vesicles formed would not pass through a 0.8 μm filter. Upon sonication for 6 minutes in a Branson sonicator, the lipid membrane structures attained the size of normal multilamellar vesicles, passing through a 0.45 μm filter. Upon sonification for an additional 6 minutes, the structures were reduced enough in size to pass through a 0.2 μm filter.

EXAMPLE 2

In this Example, a larger scale test was made using the same materials as Example 1, employing three grams of lipid. The molar proportions of the material used, as well as the volume of aqueous phase, are disclosed in Table 2.

TABLE 2

| Polyoxyethylene (2) cetyl ether | 33 mM |
|---|---|
| Cholesterol | 11 mM |
| Dicetyl phosphate | 1.5 mM |
| 5 mM phosphate, 150 mM NaCl, pH 7.4 | 50 ml |

The polyoxyethylene (2) cetyl ether, the cholesterol, and the dicetyl phosphate, were placed in a 25 ml syringe and heated to 40° C. The mixture was then forcibly injected, via a three-way stopcock, into 50 ml of the phosphate buffer, also at 40° C., contained in a 60 ml syringe. This process took less than 10 seconds. The resulting mixtures were then forced into a second 60 ml syringe at a flow rate of 8–12 m/s through an orifice about 1 mm in diameter. The resulting mixture was driven continuously back and forth between the two 60 ml syringes for about two minutes, yielding a cream. Upon centrifugation at 10,000 rpm for 15 minutes, the lipid membrane structure was separated as a layer atop the unincorporated aqueous phase. The captured aqueous volume in different experiments was 7–20.8 ml/g lipid, an amount much greater then the 2–4 ml/g lipid generally observed for multilamellar lipid membrane structures. A 1/100 dilution of the vesicles was found to be stable against aggregation for eight months at ambient temperature.

EXAMPLE 3

In this Example, substantially the same methods were used as in Example 2 except polyoxyethylene (4) lauryl ether was used in place of the polyoxyethylene (2) cetyl ether. Since the lauryl ether is a liquid at ambient temperature, no heating was required. Three grams of total lipid was used, with the proportions given in Table 3.

TABLE 3

| Polyoxyethylene (4) lauryl ether | 33 mM |
|---|---|
| Cholesterol | 11 mM |
| Dicetyl phosphate | 1.5 mM |
| 5 mM phosphate, 150 mM NaCl, pH 7.4 | 50 ml |

After formation of the paucilamellar lipid vesicles and separation by centrifugation, the captured volume was measured and found to be 8 ml/g lipid. This is entirely surprising since the lipid vesicles formed in this experiment passed freely through a 0.2 μm filter without sonication. Because of this small size, the lauryl vesicles may have similar access to organs as do SUV's have while still allowing high captured volume and encapsulation efficiency.

EXAMPLE 4

In this Example, a macromolecule, specifically hemoglobin, was used to show encapsulation efficiency for the paucilamellar lipid vesicles of the invention. Polyoxyethylene (2) cetyl ether was used to prepare the lipid membrane structures. Table 4 lists the amounts used.

TABLE 4

| Polyoxyethylene (2) cetyl ether | 3.1 gm |
|---|---|
| Cholesterol | 0.7 gm |
| Dicetyl phosphate | 0.13 gm |
| Red cell hemolysate (10 mg Hb/ml) | 50 ml |

The red cell hemolysate was formed by lysing fresh, washed human erythrocytes in hypotonic phosphate buffer to give a hemoglobin concentration of 10 mg/ml. The lipid, cholesterol and dicetyl phosphate were placed in a 10 ml syringe and heated to 40° C. The mixture was then forcibly ejected, via a three-way stopcock, into 50 ml of the red cell hemolysate contained in a 60 ml syringe. This injection took less than 5 seconds. The resulting mixture was then forced into a second 60 ml syringe at a flow rate of 8–12 m/s through an orifice of about 1 mm. The resulting mixture was driven continuously back and forth between the two syringes for approximately 2 minutes, yielding a dark pink cream.

Seven ml of the resulting cream was mixed with 3 ml of a Ficoll-Hypaque density barrier (Pharmacia) and centrifuged at 10,000 rpm for 15 minutes. Any unincorporated hemoglobin stays in the Ficoll-Hypaque density barrier whereas hemoglobin associated with the lipid vesicles will float with the lipophilic phase to the top of the aqueous phase. The lipophilic, vesicle-containing phase was pink colored and separated from the top of the density barrier. One ml aliquots of the two fractions (the lipid phase and the density barrier phase) were dissolved in 4 ml of Soluene (0.5N quaternary ammonium hydroxide in toluene, made by Packard) and the hemoglobin content was determined by measuring the absorbance of the Soret band (420 nm). The Ficoll-Hypaque had a 0.42 O.D. while the lipid membrane structures had a 1.46 O.D., showing that about 22 mg of hemoglobin per gram lipid was associated with the lipid membrane structures. The corresponding aqueous volume uptake was approximately 8 ml/g lipid.

Gassing with moist nitrogen caused the characteristic spectral change in the hemoglobin associated with the lipid membrane structures, showing a transformation from oxyhemoglobin to deoxyhemoglobin. After reexposure to ambient oxygen, the spectral change occurred, showing a transformation back to oxyhemoglobin. This illustrates that the hemoglobin is unharmed by the encapsulation process.

The hemoglobin containing structures were kept in buffer for 11 days at 40° C. then repurified on a Ficoll-Hypaque density barrier. Seventy percent of the encapsulated hemoglobin was still found to be present in the lipid phase. In addition, the hemoglobin-containing lipid membrane structures still illustrated the deoxygenation-reoxygenation reaction. A similar experiment at 17 days showed that 62% of the hemoglobin initially incorporated was still retained and still exhibited normal deoxygenation-reoxygenation.

A similar experiment was run using 30 mg hemoglobin/ml, a three-fold increase in concentration. An expected increase in hemoglobin encapsulation, 58 mg/g lipid, was observed.

EXAMPLE 5

In this Example, a lipophilic molecule, specifically all-trans retinoic acid, was used to demonstrate the capacity of the multilamellar vesicles of this invention to encapsulate lipophilic molecules. The polyoxyethylene (2) cetyl ether was used as the lipid structural material of the vesicles. Two and a half grams total lipid was employed in the proportions given in Table 5 and the method used was that of Example 2.

TABLE 5

| Polyoxyethylene (2) cetyl ether | 33 mM |
|---|---|
| Cholesterol | 6 mM |
| Dicetyl phosphate | 1.5 mM |
| All-trans retinoic acid | 0.67 mM |
| 5 mM phosphate, 150 mM NaCl, pH 7.4 | 40 ml |

In accordance with the method of the invention, the polyoxyethylene (2) cetyl ether, cholesterol, dicetyl phosphate and all-trans retinoic acid were blended at 40° C. in a 10 ml syringe and the mixture was then forcibly injected into 40 ml 5 mM phosphate, 150 mM NaCl, pH 7.4, likewise at 40° C., in a 60 ml syringe. The mixture was then subjected to shear mixing by two minutes of injection through a 1 mm orifice into another 60 ml syringe, yielding a yellow cream.

Upon centrifugation at 15,000 rpm for 15 minutes, the lipid vesicles separated as a yellow layer atop the unincorporated aqueous phase. The isolated lipid vesicles could be diluted without further volume uptake to form a stable, homogeneous suspension. The measured incorporation of the aqueous phase into the lipid membrane structures was 18 ml/g lipid. This very high value under the conditions employed may be due to the added net negative charge contributed by the all-trans retinoic acid. The encapsulation of all-trans retinoic acid was 8 mg/g lipid (>99%).

EXAMPLE 6

In this Example, all-trans retinoic acid was used to replace dicetyl phosphate in providing the negative charge for lipid vesicles prepared with polyoxyethylene (2) cetyl and cholesterol. Two and a half grams of a lipid mixture with the molar proportions in Table 6 was employed. The method used was identical with that of Example 2.

TABLE 6

| Polyoxyethylene (2) cetyl ether | 33 mM |
|---|---|
| Cholesterol | 6 mM |
| All-trans retinoic Acid | 1.5 mM |
| 5 mM phosphate, 150 mM NaCl, pH 7.4 | 40 ml |

After formation of the paucilamellar vesicles and separation by centrifugation, the aqueous volume taken up was measured and found to be 12 ml/g lipid. The all-trans retinoic acid encapsulated was 17.5 mg/g lipid.

EXAMPLE 7

This Example demonstrates the capacity of lipid vesicles formed of polyoxyethylene (2) cetyl ether to incorporate a different lipophilic material, the insect repellant N,N-diethyl meta-toluamide. Two and a half gram of lipid was used in the proportions given in Table 7. The method used was the same as Example 5 with the N,N-diethyl meta-toluamide replacing the all-trans retinoic acid.

TABLE 7

| Polyoxyethylene (2) cetyl ether | 33 mM |
|---|---|
| N,N-diethyl meta-toluamide | 11 mM |
| Cholesterol | 5 mM |
| Dicetyl phosphate | 1.5 mM |

TABLE 7-continued

| 5 mM phosphate, 150 mM NaCl, pH 7.4 | 40 ml |
|---|---|

Upon centrifugation at 15,000 rpm for 15 minutes, the lipid membrane structures separated as a white layer atop the unincorporated aqueous phase. The structures could readily be redispersed and diluted into a uniform suspension without separation of a low density phase of N,N-diethyl meta-toluamide. The volume uptake was 10 ml/g lipid and >99% of the N,N-diethyl meta-toluamide was retained by the lipid membrane vesicle. Separate experiments showed that if cholesterol is eliminated from the system, the liposomes quickly lost the N,N-diethyl meta-toluamide.

EXAMPLE 8

This Example demonstrates the capacity of the lipid vesicles formed by the method of the invention to encapsulate supramacromolecular structures, specifically avian encephalitis (AE) virus, a' 17 nm virion. The proportions and method used are identical to those of Example 4 except the red blood lysate was replaced by a solution of the AE virus. The results are shown in Table 8.

TABLE 8

| Serum Dilution | 1:00 | 1:2 | 1:4 | 1:8 | 1:16 | 1:32 |
|---|---|---|---|---|---|---|
| Sample AE virus | 1.47 | 0.75 | 0.48 | 0.24 | 0.21 | 0.17 |
| Aqueous residue | 0.08 | 0.08 | 0.10 | 0.08 | 0.12 | 0.99 |
| Standard-control | 1.39 | 0.67 | 0.40 | 0.16 | 0.13 | 0.09 |
| Residue-control | 0.00 | 0.00 | 0.02 | 0.00 | 0.04 | 0.02 |

As is evident from the results of Table 8, at least 75% of AE is taken up into the paucilamellar vesicles of this invention until the amount of virus becomes too small, indicating the potential usefulness of these vesicles in the transportation of viruses and plasmids. Conventional MLV's or LUV's could not be used to stably encapsulate this large a molecule. Similar tests have been carried out with a Herpes virus (Marek's disease), having a diameter of about 0.15 $\mu$ instead of 0.017 $\mu$. Again, the method disclosed allowed high encapsulation efficiency.

EXAMPLE 9

This Example is based on the use of glyceryl monostearate as the surfactant (lipid) for making the paucilamellar lipid vesicles. The glyceryl monostearate was mixed with cholesterol and oleic acid was added as a negative charge producing material. The molar ratios of glyceryl monostearate cholesterol/oleic acid was of 1:0.2:0.09. The methods used were those of Example 2. Table 9 gives the exact proportions used. The lipid phase was heated to about 75° C. to get dissolution. Batches were prepared, 60 ml at a time, by blending the heated glyceryl monostearate/cholesterol/oleic acid lipophilic phase with a three-fold greater volume of Dulbecco phosphate-buffered saline.

TABLE 9

| Glyceryl monostearate | 50.2 g | 139 mmol |
|---|---|---|
| Cholesterol | 10.2 g | 28 mmol |
| Oleic acid | 5.4 g | 12 mmol |

The lipid vesicles were separated by centrifugation and the vesicles were measured to be about 1–3 $\mu$ in diameter. The prepared lipid vesicles were stored for approximately sixteen hours in a six-fold volume excess of buffer, and after an additional sixteen hours, the vesicles were diluted again with buffer to a total volume of 1,050 ml.

This dilution resulted in a relatively non-viscous solution which by gradient centrifugation was approximately 65% vesicle by volume. The volume uptake was 8.9 ml/g lipid.

The lipid vesicles produced showed substantial stability in 0.5 molar hydrochloric acid, indicating that they could be useful for enteric applications. In addition, glyceryl monostearate is on the FDA approved list of materials, oleic acid is an accepted food additive, and cholesterol is an unavoidable food.

Replacing the oleic acid with dicetyl phosphate or palmitic acid can lead to even higher water uptake. Using the dicetyl phosphate to make the vesicles (without having cholesterol in the mixture) yields a water uptake of 11.0 ml/g lipid, while using the palmitic acid and cholesterol in the lipophilic phase yields a still higher water uptake, 15 ml/g lipid. In all experiments with glyceryl monostearate, water uptake proceeded over several hours.

EXAMPLE 10

This Example illustrates that polyoxyethylene (9) glyceryl stearate is also useful to form the paucilamellar lipid vesicles of the invention. Table 10 lists the ingredients and amounts used to form the lipophilic phase of the vesicles of this Example. As with the glyceryl monostearate, the mixture had to be heated to about 70° C. to obtain a clear solution. After dissolution of the cholesterol and oleic acid in the ester, the solution was cooled to about 45° C. for use.

TABLE 10

| | | |
|---|---|---|
| Polyoxyethylene (9) glyceryl stearate | 62.5 g | 70 mmol |
| Cholesterol | 5.0 g | 14 mmol |
| Oleic acid | 0.9 g | 3 mmol |

Ten ml of the lipid mixture was combined with 50 ml of a phosphate saline buffer, using the syringe method described in Example 2 and a smooth cream of lipid vesicles was obtained. Approximately 5 ml of the cream was combined with 5 ml of Ficoll/Hypaque gradient and centrifuged at 1500 rpm's for approximately one hour. The water uptake was determined to be about 6 ml/g lipid. Microscopy shows that the lipid vesicles are in the 1-3 $\mu$ range.

EXAMPLE 11

In this Example, two other polyoxyethylene esters, polyoxyethylene (3) stearate and polyoxyethylene (9) stearate were tested to see if they would form the paucilamellar lipid vesicles of the invention. Using the procedures as described in Example 1, the polyoxyethylene (3) stearate was blended with dicetyl phosphate and cholesterol to form the lipid phase. The resulting lipid mixture was shear mixed with a phosphate buffer, forming the lipid vesicles. The ratio of ester/cholesterol/dicetyl phosphate was 1/0.33/0.01. Lipid vesicles formed using the polyoxyethylene (3) stearate had a water uptake of 6.5 ml/g of lipid. If the dicetyl phosphate and cholesterol are not used, a granular suspension rather than a dispersion of lipid vesicles is produced.

Identical tests were run using polyoxyethylene (9) stearate in place of the polyoxyethylene (3) stearate. Heterogeneous lipid vesicles were formed without the dicetyl phosphate and cholesterol with the polyoxyethylene (9) stearate; however, it was not possible to separate the lipid vesicles using density gradient centrifugation. The addition of cholesterol and dicetyl phosphate to the lipid leads to a smooth suspension of well defined lipid vesicles. The water uptake, is measured by polymer density gradient centrifugation, was 6.5 ml/g lipid.

EXAMPLE 12

In this Example, a variety of polyoxyethylene sorbitan esters were tested to determine whether any would form the paucilamellar lipid vesicles of the invention. The polyoxyethylene ("POE") sorbitan esters are available from ICI, Americas, Wilmington, Del., under the trade name TWEEN. As is evident, only some of these sorbitan esters will form lipid vesicles. One theory for this finding is that a certain of hydrophobic/hydrophilic character or balance is necessary to form the vesicles of the invention.

Five different polyoxyethylene sorbitan esters were tested:
polyoxyethylene (20) sorbitan monooleate
polyoxyethylene (20) sorbitan trioleate
polyoxyethylene (20) sorbitan monoplamitate
polyoxyethylene (20) sorbitan monostearate
polyoxyethylene (5) sorbitan monooleate All of these surfactants were used in two different formulations: a first formulation with just 1 mol% dicetyl phosphate (DP) and a second formulation with 1 mol% dicetyl phosphate and 33 mol% cholesterol (DPC).

Table 11 shows the results of this experiment. A positive indication (+) in the column vesicle formation indicates formation of discrete lipid vesicles while a negative (−) indicates that no lipid vesicles were observed.

TABLE 11

| Surfactant | Additives | Vesicle Formation |
|---|---|---|
| POE (20) sorbitan monooleate | DP | − |
| POE (20) sorbitan monooleate | DPC | + |
| POE (20) sorbitan trioleate | DP | − |
| POE (20) sorbitan trioleate | DPC | + |
| POE (20) sorbitan monopalmitate | DP | − |
| POE (20) sorbitan monopalmitate | DPC | − |
| POE (20) sorbitan monostearate | DP | − |
| POE (20) sorbitan monostearate | DPC | − |
| POE (5) sorbitan monooleate | DP | − |
| POE (5) sorbitan monooleate | DPC | − |

The polyoxyethylene (20) sorbitan monooleate gave a water uptake (as measured by polymer density gradient centrifugation), of 5.0 ml/g lipid while the polyoxyethylene sorbitan trioleate with dicetyl phosphate and cholesterol yielded visible liposomes which passed through 0.2 $\mu$ filters and had a water uptake of 8.0 ml/g lipid. The failure of the other materials to form lipid vesicles is indicative of differences in head groups and hydrophobic tails.

EXAMPLE 13

This Example illustrates that certain diethanolamines can be used to form the paucilamellar lipid vesicles of the invention. Three different diethanolamines were tested: diethanolamine lauramide ($C_{12}$), diethanolamine myristamide ($C_{14}$) and diethanolamine linoleamide ($C_{18}$-two unsaturations). All of the testing was done as described in Example 2 except the diethanolamine was substituted for the polyoxyethylene (2) cetyl ether.

Table 12 shows the results of this testing. The column entitled "-C, -DCP" shows the results testing using the surfactant alone, the column entitled "C" shows the results for a surfactant with a 4:1 blend of surfactant and cholesterol, and the column entitled "DCP" shows the results with 1 mol% dicetyl phosphate added in addition to the cholesterol and surfactant.

TABLE 12

| Surfactant | Water Uptake (ml/g) | | |
|---|---|---|---|
| | -C, -DCP | C | DCP |
| Diethanolamine lauramide | 2.0 | 4.5 | 5.5 |
| Diethanolamine myristamide | 3.0 | 5.5 | 5.5 |
| Diethanolamine linoleamide | 3.5 | 8.0 | 8.5 |

As is evident from Table 12, all of these surfactants yield high levels of water uptake with cholesterol, particularly with the negative charge-producing dicetyl phosphate added, showing the formation of paucilamellar lipid vesicles. Other diethanolamines which have been tested, e.g., stearyl diethanolamine, do not show this type of water uptake.

EXAMPLE 14

In this Example, the incorporation of a lipophilic photosensitizer, hematoprotoporphyrin (sodium salt) was tested for incorporation into diethanolamine linoleamide lipid vesicles. Five mg of the porphyrin was dissolved in 0.5 g of warm diethanolamine linoleamide. Cholesterol and dicetyl phosphate were added and the syringe procedure of Example 2 was used, with 2 ml of 0.02M Tris hydrochloride buffer as the aqueous phase. The resulting lipid vesicles were separated on a Ficoll/Hypaque density gradient centrifugation for ten minutes and the porphyrin content was determined by absorbance in the Soret region. Table 13 gives the uptake per gram of lipid for buffer, hematoprotoporphyrin, and the percentage of the hematoprotoporphyrin offered. This Example illustrates that the paucilamellar lipid vesicles of the invention can be used to encapsulate a lipophilic porphyrin compound.

TABLE 13

| Uptake/g Diethanolamine Linoleamide | Buffer (ml) | Hematoprotoporphyrin | |
|---|---|---|---|
| | | (mg) | (% of offered) |
| | 5.6 | 4.3 | 86 |

EXAMPLE 15

This Example illustrates encapsulation of large molecules or colloids, e.g., pigments in oil carriers, into the central cavity of the paucilamellar lipid vesicles. Four different pigments were tested: a yellow concentrate of cadmium sulfate and barium sulfate, a blue concentrate of ferric ferricyanide, a red concentrate of dihydroanthaquinone on aluminum hydrate, and a green concentrate of chromium hydroxide. Approximately 100 mg of each concentrate was dispersed in 0.2 ml of linseed oil and blended with 0.2 ml of 1/0.33/0.01 polyoxyethylene (2) cetyl ether/cholesterol/dicetyl phosphate lipid phase at 40° C. The oil/surfactant mixture was sonicated for approximately 15 seconds to disperse the oil throughout the surfactant and then placed into a syringe. The lipid vesicles were made using the syringe method of Example 1 by shear mixing the oil/surfactant dispersion with 1.0 ml of water. The resulting lipid vesicles were centrifuged and separated on a Ficoll/Hypaque gradient.

The yellow concentrate yielded a heterogeneous population of lipid vesicles between 5 and 15 $\mu$ in diameter, some of which were distinctly yellow in the interior. Many of the lipid vesicles appeared to have 1-2 $\mu$ inclusion bodies entrapped in the interior cavity. No free oil was discovered.

Similarly, the blue concentrate yielded a heterogeneous population of oil-filled lipid vesicles with 2-15 $\mu$ diameters. Again, there was no free oil. The larger lipid vesicles also showed inclusion bodies about 1 $\mu$ in diameter. Although there was a yellow pellet from the yellow concentrate discussed above, there was no pellet from the blue concentrate.

The green concentrate yielded green-colored lipid vesicles but again no pellet was uncovered. Some of the lipid vesicles appeared to have some form of reticular network inside. There were also some inclusion bodies within the cavity of up to 5 $\mu$ size.

The red concentrate also yielded lipid vesicles without a pellet or free oil. The reticular network was very prominent inside the lipid vesicles central cavity.

These experiments clearly show that large particles, in fact, particles the size of classic lipid vesicles, can be incorporated into the oil-filled cavity of the present paucilamellar lipid vesicles.

EXAMPLE 16

In this Example, a number of different polyoxyethylene surfactants were tested for oil uptake and paucilamellar lipid vesicle formation. The syringe method of Example 1 was used, with 0.4 g of surfactant being blended with 1.5 g of mineral oil and the resulting lipid phase being blended with 1.5 g of water. Polyoxyethylene (4) stearyl ether was tested in two formulations, one with and one without cholesterol. Without cholesterol, a solid aggregate of surfactant was formed while with cholesterol, heterogeneous lipid vesicles were formed. These lipid vesicles appeared to be multilamellar, not paucilamellar lipid vesicles. In fact, less than one-third of the mineral oil was taken up.

In contrast, when polyoxyethylene (20) stearyl ether was used, more than 90% of the oil was taken up into the vesicle even without the use of the cholesterol. Similar positive results were obtained with diethanolamine lauramide, and diethanolamine myristamide.

As can be seen from the results of these Examples, paucilamellar lipid vesicles having high water or oil uptake can be formed with the materials and methods of the present invention. Other testing has shown that if different methods are used, e.g., the Bangham method for manufacture of lipid vesicles, paucilamellar lipid vesicles are not formed using the same materials but rather classic multilamellar lipid vesicles are formed. These MLV's yield at least a 30% lower water uptake as compared with PLV's and they exhibit substantially no oil uptake.

The foregoing description is illustrative only and those skilled in the art may find other materials and methods which accomplish the same results. Such other materials and methods are included within the following claims.

What is claimed is:

1. A method of making paucilamellar lipid vesicles having 2 to 8 exterior lipid bilayers surrounding a large, amorphous, substantially aqueous filled center comprising the steps of:

A. forming a lipophilic phase of a surfactant and any lipid soluble materials to be incorporated into said lipid vesicles, said surfactant being selected from a group consisting of polyoxyethylene fatty esters having the formula $$R_1\text{—COO}(C_2H_4O)_n H$$

where $R_1$ is a radical of lauric, myristic, cetyl, stearic, or oleic acid and $n=2\text{–}10$;

polyoxyethylene fatty acid ethers, having the formula $$R_2\text{—CO}(C_2H_4O)_m H$$

where $R_2$ is a radical of lauric, myristic, or cetyl acids, single or double unsaturated octadecyl acids, or double unsaturated eicodienoic acids and m ranges from 2–4;

polyoxyethylene (20) sorbitan mono- or trioleate; and polyoxyethylene glyceryl monostearate with 1–10 polyoxyethylene groups;

B. forming an aqueous phase of an aqueous solution and any aqueous soluble material to be incorporated into said lipid vesicles; and C. blending said lipophilic phase and said aqueous phase in a single step under shear mixing conditions.

2. The method of claim 1 wherein said lipophilic phase further comprises a steroid.

3. The method of claim 2 wherein said steroid comprises a sterol selected from the group consisting of cholesterol and hydrocortisone.

4. The method of claim 1 wherein said lipophilic phase further comprises a charge-producing agent.

5. The method of claim 4 wherein said charge-producing agent is a negative charge-producing agent selected from a group consisting of oleic acid, dicetyl phosphate, cetyl sulphate, phosphatidic acid, phosphatidyl serine, and mixtures thereof.

6. A method of encapsulating aqueous soluble materials in paucilamellar lipid vesicles comprising the steps of:

forming a lipophilic phase of a surfactant and any other materials which are soluble in said surfactant by dissolving said other materials in said surfactant, said surfactant being selected from a group consisting of polyoxyethylene fatty esters having the formula $$R_1\text{—COO}(C_2H_4O)_n H$$

where $R_1$ is a radical of lauric, myristic, cetyl, stearic, or oleic acid and $n=2\text{–}10$;

polyoxyethylene fatty acid ethers, having the formula $$R_2\text{—CO}(C_2H_4O)_m H$$

where $R_2$ is a radical of lauric, myristic, or cetyl acids, single or double unsaturated octadecyl acids, or double unsaturated eicodienoic acids and m ranges from 2–4;

polyoxyethylene (20) sorbitan mono- or trioleate; and polyoxyethylene glyceryl monostearate with 1–10 polyoxyethylene groups;

forming an aqueous phase by dissolving said aqueous soluble materials to be encapsulated and any other aqueous dissolvable materials in an aqueous solvent;

blending said aqueous phase and said lipophilic phase in a single step under shear mixing conditions in order to form said paucilamellar lipid vesicles; and separating said paucilamellar lipid vesicles from the blend of said aqueous phase and said lipophilic phase.

7. The method of claim 6 wherein said lipophilic phase further comprises a steroid.

8. The method of claim 7 wherein said steroid comprises a sterol selected from the group consisting of cholesterol and hydrocortisone.

9. The method of claim 6 wherein said lipophilic phase further consists of a charge-producing agent.

10. The method of claim 9 wherein said charge-producing agent is selected from a group consisting of oleic acid, dicetyl phosphate, cetyl sulphate, phosphatidic acid, phosphatidyl serine, and mixtures thereof.

11. A method of making paucilamellar lipid vesicles having 2 to 8 exterior lipid bilayers surrounding a large, amorphous, substantially aqueous filled center comprising the steps of:

A. forming a lipophilic phase of a surfactant and any lipid soluble materials to be incorporated into said lipid vesicles, said surfactant being selected from a group consisting of diethanolamides having the formula $$(\text{HOCH}_2\text{—CH}_2)_2\text{NCO—}R_3$$

where $R_3$ is a radical of caprylic, lauric, myristic or linoleic acids;

long chain acyl hexosamides having the formula $$R_4\text{—NHCO—}(CH_2)_b\text{—CH}_3$$

where b ranges from 10–18 and $R_4$ is a radical of a sugar molecule selected from a group consisting of glucosamine, galactosamine, and N-methylglucamine; and long chain acyl amino acid amides having the formula $$R_5\text{—CH(COOH)—NHCO—}(CH_2)_c\text{—CH}_3$$

where c ranges from 10–18 and $R_5$ is a radical of an amino acid side chain;

long chain acyl amides having the formula $$\text{HOOC—}(CH_2)_d\text{—N}(CH_3)\text{—}(CH_2)_3\text{—NHCO—}R_6$$

where $R_6$ is an acyl chain having 12–20 carbons and not more than two unsaturations, and d ranges from 1–3;

and glycerol monostearate;

B. forming an aqueous phase of an aqueous solution and any aqueous soluble material to be incorporated into said lipid vesicles; and C. blending said lipophilic phase and said aqueous phase in a single step under shear mixing conditions.

12. The method of claim 11 wherein said lipophilic phase further comprises a steroid.

13. The method of claim 12 wherein said steroid comprises a sterol selected from a group consisting of cholesterol and hydrocortisone.

14. The method of claim 11 wherein said lipophilic phase further comprises a charge-producing agent.

15. The method of claim 14 wherein said charge-producing agent is selected from a group consisting of oleic acid, dicetyl phosphate, cetyl sulphate, phosphatidic acid, phosphatidyl serine, and mixtures thereof.

16. A method of encapsulating aqueous soluble materials in paucilamellar lipid vesicles comprising the steps of:

forming a lipophilic phase of a surfactant and any other materials which are soluble in said surfactant by dissolving said other materials in said surfactant, said surfactant being selected from a group consisting of diethanolamides having the formula $$(HOCH_2-CH_2)_2NCO-R_3$$

where $R_3$ is a radical of caprylic, lauric, myristic or linoleic acids;

long chain acyl hexosamides having the formula $$R_4-NHCO-(CH_2)_b-CH_3$$

where b ranges from 10–18 and $R_4$ is a radical of a sugar molecule selected from a group consisting of glucosamine, galactosamine, and N-methylglucamine;

long chain acyl amino acid amides having the formula $$R_5-CH(COOH)-NHCO-(CH_2)_c-CH_3$$

where c ranges from 10–18 and $R_5$ is an amino acid side chain;

long chain acyl amides having the formula $$HOOC-(CH_2)_d-N(CH_3)-(CH_2)_3-NHCO-R_6$$

where $R_6$ is an acyl chain having 12–20 carbons and not more than two unsaturations, and d ranges from 1–3;

and glycerol monostearate;

forming an aqueous phase by dissolving said materials to be encapsulated and any other aqueous dissolvable materials in an aqueous solvent;

blending said aqueous phase and said lipophilic phase in a single step under shear mixing conditions in order to form said paucilamellar lipid vesicles; and separating said paucilamellar lipid vesicles from the blend of said aqueous phase and said lipophilic phase.

17. The method of claim 16 wherein said lipophilic phase further comprises a steroid.

18. The method of claim 17 wherein said steroid is selected from a group consisting of cholesterol and hydrocortisone.

19. The method of claim 16 wherein said lipophilic phase further consists of a charge-producing agent.

20. The method of claim 19 wherein said charge-producing agent is selected from a group consisting of oleic acid, dicetyl phosphate, cetyl sulphate, phosphatidic acid, phosphatidyl serine, and mixtures thereof.

21. Paucilamellar lipid vesicles consisting of 2 to 8 lipid bilayers in the form of substantially spherical shells separated by aqueous layers surrounding a large, amorphous, substantially aqueous filled central cavity, said lipid bilayers comprising a surfactant selected from a group consisting of diethanolamides having the formula $$(HOCH_2-CH_2)_2NCO-R_3$$

where $R_3$ is a radical of caprylic, lauric, myristic or linoleic acids;

long chain acyl hexosamides having the formula $$R_4-NHCO-(CH_2)_b-CH_3$$

where b ranges from 10–18 and $R_4$ is a radical of a sugar molecule selected from a group consisting of glucosamine, galactosamine, and N-methylglucamine;

long chain acyl amino acid amides having the formula $$R_5-CH(COOH)-NHCO-(CH_2)_c-CH_3$$

where c ranges from 10–18 and $R_5$ is an amino acid side chain; and long chain acyl amides having the formula $$HOOC-(CH_2)_d-N(CH_3)-(CH_2)_3-NHCO-R_6$$

where $R_6$ is an acyl chain having 12–20 carbons and not more than two unsaturations, and d ranges from 1–3.

22. The paucilamellar lipid vesicles of claim 21 wherein said lipid bilayers further comprise a steroid.

23. The paucilamellar lipid vesicles of claim 22 wherein said steroid is selected from a group consisting of cholesterol and hydrocortisone.

24. The paucilamellar lipid vesicles of claim 21 wherein said lipid bilayers further comprise a charge-producing agent.

25. The paucilamellar lipid vesicles of claim 24 wherein said charge-producing agent is selected from a group consisting of oleic acid, dicetyl phosphate, cetyl sulphate, phosphatidic acid, phosphatidyl serine, and mixtures thereof.

* * * * *